United States Patent
Koontz et al.

[19]

[11] Patent Number: 5,963,660
[45] Date of Patent: *Oct. 5, 1999

[54] METHOD AND APPARATUS FOR DETECTING AND MEASURING LAPS AND GAPS IN COMPOSITE MATERIALS

[75] Inventors: Jan S. Koontz, Enumclaw; Robert E. Cranfill, Seattle, both of Wash.

[73] Assignee: The Boeing Company, Seattle, Wash.

[*] Notice: This patent is subject to a terminal disclaimer.

[21] Appl. No.: 08/719,694

[22] Filed: Sep. 26, 1996

[51] Int. Cl.$^6$ .............................. G01B 9/00; B32B 31/00
[52] U.S. Cl. ...................... 382/141; 382/173; 382/286; 156/64; 264/40.1
[58] Field of Search ............................. 382/108, 141, 382/152, 173, 274, 286; 348/86, 92, 88, 125; 356/384, 372, 237; 428/293.7, 608; 257/746; 250/559.05, 559.08, 559.19, 559.29, 559.42, 559.46; 364/468.17, 469.01, 475.09, 507, 559, 560, 561; 156/64; 264/40.1; 162/198, 263

[56] References Cited

U.S. PATENT DOCUMENTS

| | | | |
|---|---|---|---|
| 4,277,178 | 7/1981 | Cushing et al. | 356/431 |
| 4,460,921 | 7/1984 | Henry et al. | 358/107 |
| 4,551,768 | 11/1985 | Tsuchiya et al. | 358/283 |
| 4,864,150 | 9/1989 | Mann et al. | 250/571 |
| 4,876,457 | 10/1989 | Bose | 250/563 |
| 5,120,976 | 6/1992 | Clayton et al. | 250/564 |
| 5,268,580 | 12/1993 | He | 250/566 |
| 5,317,387 | 5/1994 | Van Hengel et al. | 356/372 |
| 5,341,436 | 8/1994 | Scott | 382/141 |
| 5,352,878 | 10/1994 | Smith et al. | 235/462 |
| 5,404,003 | 4/1995 | Smith | 235/462 |
| 5,412,197 | 5/1995 | Smith | 235/462 |
| 5,562,788 | 10/1996 | Kitson et al. | 156/64 |
| 5,622,602 | 4/1997 | Yakabe et al. | 162/252 |
| 5,709,775 | 1/1998 | Trokhan et al. | 162/117 |

FOREIGN PATENT DOCUMENTS

PCT/NL90/
00045  11/1990  WIPO.

OTHER PUBLICATIONS

Bouton, Gary and Barbara, *Inside Adobe Photoshop for Windows*, pp. i–iii (1994); ISBN 1–56205–259–4.

Bouton, Gary and Barbara, *Inside Adobe Photoshop for Windows*, Chapter 2: The Digital Image, pp. 46–85 (1994); ISBN 1–56205–259–4.

Bouton, Gary and Barbara, *Inside Adobe Photoshop for Windows*, Chapter 3: The PhotoCD, pp. 84–115 (1994); ISBN 1–56205–259–4.

Lee Kitson and Denny Rock, Tow Gap Detection Using Laser Images, American Helicopter Society, Proceedings: Technical Specialists' Meeting Rotorcraft Composites Manufacturing Transition into the 21st Century, pp. 1–13, Sep. 1993.

S. Toll & P.O. Anderson, Microstructural Characterization of Injection Moulded Composites Using Image Analysis, Composites, vol. 22, Jul. 1991, pp. 298–306.

Bruce F. Blumentritt, Ban T. Vu, Stuart L. Cooper, The Mechanical Properties of Oriented Discontinuous Fiber–Reinforced Thermoplastics, Polymer Engineering & Science, Sep. 1974, vol. 14, No. 9, pp. 633–640.

*Primary Examiner*—Leo H. Boudreau
*Assistant Examiner*—Brian P. Werner
*Attorney, Agent, or Firm*—Christensen O'Connor Johnson & Kindness PLLC

[57] ABSTRACT

An electronic scanner having a light source and a light sensitive head is connected via a cable to a computer. The scanner head detects reflected light from the surface of the composite material and generates an electronic representation of the surface. A conventional software driver interprets the scanner output to produce an electronic bit-mapped image. The electronic image is then displayed so that gaps are readily visible. The electronic representation is also analyzed to determine the presence of laps and gaps, to measure gap widths, to measure the distance between points on the display, and to determine the percentage of the surface covered by fiber material. The electronic representation may also be stored for later analysis.

4 Claims, 9 Drawing Sheets

| MEASURED GAP WIDTH (F) | MEASURED FIBER WIDTH (T) |
|---|---|
| 1 | 90 |
| 8 | 50 |
| 25 | 129 |

| SYNTHESIZED GAP WIDTH | SYNTHESIZED FIBER WIDTH |
|---|---|
| 1 | 45 |
| * | 45 |
| 8 | 50 |
| 25 | 43 |
| * | 43 |
| * | 43 |

METHOD AND APPARATUS FOR DETECTING AND MEASURING LAPS AND GAPS IN COMPOSITE MATERIALS

FIELD OF THE INVENTION

This invention generally relates to a method and apparatus for detecting and measuring gaps and laps in the surface of a lay-up of composite material.

BACKGROUND OF THE INVENTION

Composite materials are increasingly used in the manufacturing process for a wide variety of products that require a high strength-to-weight ratio. A composite is a material made up of two or more components that confer different types of strength or resilience. For example, carbon fibers having a high tensile strength are embedded in an epoxy resin. The combination produces a material that may be formed to a wide variety of shapes and which, pound for pound, is many times stronger than steel.

In a typical composite manufacturing process, many long strands of carbon or other fibers are pulled from spools and aligned so that they are parallel. The parallel band of fibers is then applied and pressed to a heated surface and held in place with an epoxy resin. Because the resulting composite material is strongest in the direction that the fibers run, several layers of fibers are applied in the composite manufacturing process. In this layering, or laminating, process layers of composite fibers are applied so that the fibers in successive layers run transversely of the fibers of preceding layers to produce a material that is strong in every direction. Once the composite has been built up, it is heat cured in a kiln or autoclave, producing a rigid structure.

Although the composite laminate process is extremely effective at producing strong, lightweight materials, problems can occur in the manufacturing process that affect the strength of the resulting material. First, gaps can occur between the carbon fibers that are applied to the surface. Such gaps are especially likely to occur when producing a composite device having numerous bends, folds, or curves. The presence of gaps of significant size can weaken the resulting composite material in the area of the gaps. This weakness is compounded when there are multiple gaps in the same general vicinity. Similarly, fibers that are intended to be adjacent and parallel may overlap one another. The overlapping fibers, or "laps", also create an area of decreased strength. The presence of a lap may even be worse than the presence of a gap. Because the fibers expand during the heat curing process, gaps below a certain size will become filled as the fibers expand and shift toward one another. A lap, however, is likely to worsen during the curing process. An overlapping fiber will typically remain in place but will become stretched as the fibers expand during the curing process. As a result, a lap creates a weak area in the composite material in the vicinity of the lap.

To avoid these weakened areas in the finished material, each layer of fibers must be inspected for laps and gaps. Typically, inspectors visually survey the surface of a composite material looking for laps and gaps. This is an especially tedious process that is prone to error. Because the fibers and gaps are small, a magnifying glass must be used to search for laps and gaps. In addition, because carbon fibers are black, it is particularly difficult to visually find a lap or gap in the top layer of fibers when the layer of fibers below it is also black. Moreover, it is difficult to precisely measure the size of a gap between fibers, making it difficult to determine whether an identified gap is sufficiently large to pose a problem. These problems are compounded when the composite material being manufactured is large. An inspector searching the surface of a large composite material is prone to fatigue and eye strain and is likely to miss significant laps and gaps.

SUMMARY OF THE INVENTION

The present invention provides a simple and effective method and apparatus for surveying the surface of a composite material to find flaws such as laps and gaps in the fibers. In the preferred embodiment, an electronic scanner of the type normally used to digitize documents is passed over the surface to be surveyed. The scanner includes a head having a light source that illuminates the surface of the composite material and a light sensitive section or detector to detect reflections. By scanning the surface in the direction of the fibers, the presence of gaps and laps in the surface layer is detected. This method is capable of quantifying the size of the laps or gaps and the distance between nearby laps or gaps so that a manufacturer can determine whether the composite material will be significantly weakened because of the presence of the laps or gaps.

In accordance with other aspects of this invention, the optically scanned surface image may be displayed in a form that will make the laps and gaps visible. In the preferred embodiment, the scanned image may be graphically displayed on a computer terminal display.

In accordance with further aspects of this invention, the size of a lap or gap may be determined and represented on the display. Similarly, the distance between a lap or gap and another lap, gap, or other point on the surface may be determined and displayed.

In accordance with still other aspects of this invention, the scanning resolution may be adjusted to accommodate a range of fiber sizes and possible gap widths.

In accordance with yet other aspects of this invention, the scanned images and lap and gap data may be stored in a memory for later display or analysis. Similarly, images or data representations of images may be retrieved from a memory to analyze the images for laps or gaps.

In accordance with further aspects of this invention, scanned images may be analyzed to determine the percentage of the surface area that is covered by the fibers of the topmost layer.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 8A is an exemplary width data array;

FIG. 8B is an exemplary synthesized width data array;

DETAILED DESCRIPTION OF THE PREFERRED EMBODIMENT

Figure 1:
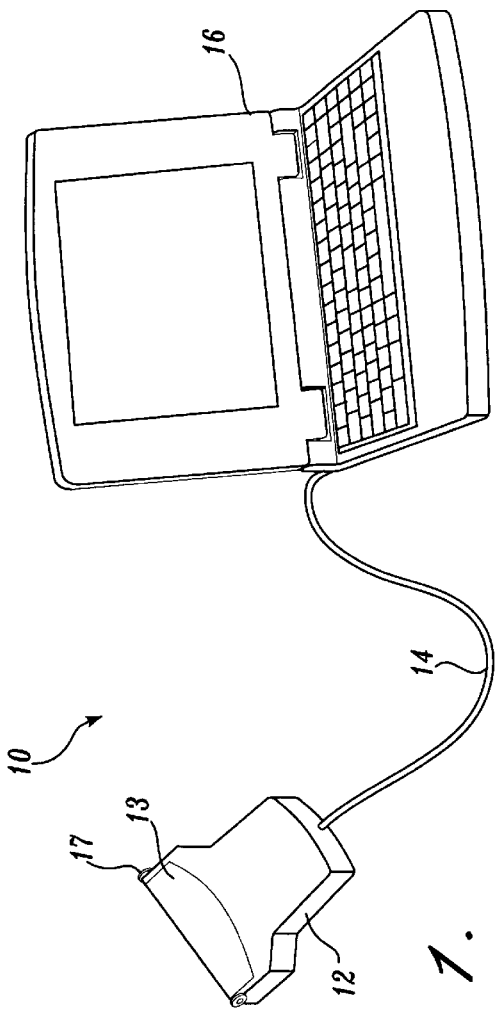
FIG. 1 is a diagrammatic top perspective of a lap and gap detecting apparatus in accordance with the present invention.
Figure 2:
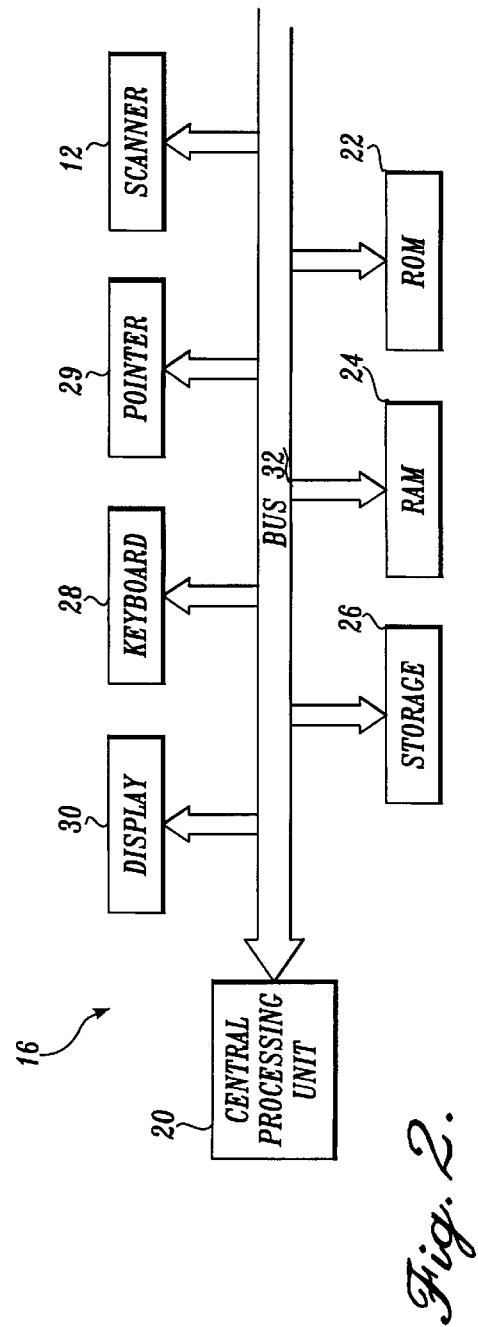
FIG. 2 is a block diagram of components of the lap and gap detecting apparatus of FIG. 1.

Referring to FIG. 1, a lap/gap detector configured in accordance with the present invention is indicated generally by the reference numeral 10. An electronic document scanner 12 that includes a head 13 having a light source and a light sensitive portion is connected via a cable 14 to a generally conventional desktop or notebook computer 16. Several of the key components of the computer 16 are illustrated in FIG. 2. Although it will be apparent to those of ordinary skill in the art that the computer 16 includes many more components than those shown in FIG. 2, a disclosure of the preferred embodiment for practicing the present invention does not require all of these generally conventional components to be shown.

A CPU 20 is coupled through a bus 32 to a ROM 22 and a RAM 24. The CPU 20 responds to program instructions stored in the ROM and temporarily in the RAM. The computer 16 also includes a storage device 26, such as a hard disk drive, floppy disk drive, or other storage media. A keyboard 28 and a pointer 29 are coupled to the CPU 20 through the bus 32. The pointer 29 is a mouse, trackball, or other device that enables a user to instruct the CPU by interacting with a display 30. According to the present invention, the CPU is programmed to process the data provided by the scanner 12 which is also coupled to the CPU through the bus 32. The data processed by the CPU is also displayed on the display 30 and can be stored in the storage 26 for later use.

Figure 3A:
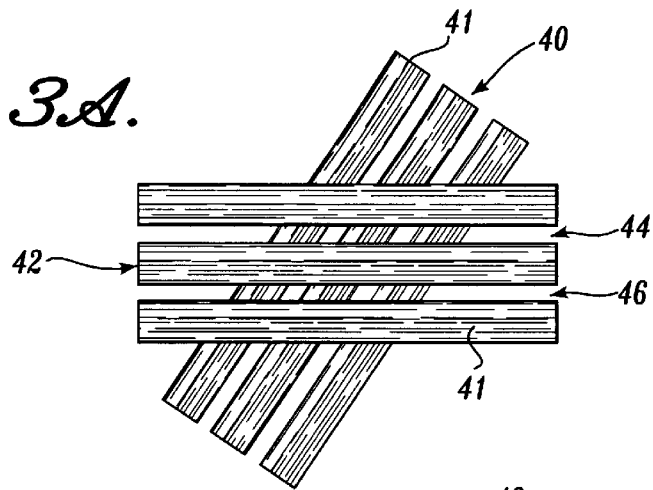
FIG. 3A is a diagrammatic top plan of two layers of composite fiber materials with gaps present in the surface layer.

A composite laminate material that may be scanned and analyzed for laps and gaps in accordance with the present invention is represented in FIG. 3A. A lower layer 40 of composite material is composed of numerous fibers 41 embedded in epoxy resin. For an aircraft flight control surface or fairing, typically the fibers 41 are approximately ⅛ inch thick. The fibers 41 on each layer are applied several fibers at a time in a parallel band. Although any number of fibers 41 may be applied at once, they are often applied in bands of 12, 24, or 32 fibers. Similarly, the composite lay-up may be constructed from bands of tape rather than bands of parallel fibers. A surface layer 42 of composite material is placed over the top of the lower layer 40 such that the fibers 41 of the surface layer 42 extend transversely of the fibers 41 of the lower layer. While only two layers are depicted in FIG. 3A, those skilled in the art will recognize that any number of layers may be used consistent with the present invention.

Although ideally there are no gaps in each layer, the surface layer 42 is shown containing two gaps 44, 46. To the naked eye, the gaps 44, 46 are visible but difficult to find because the gaps are small and each layer of composite material is black. Thus, in accordance with the present invention, the head 13 of the scanner 12 is passed across the surface layer 42 in a direction substantially parallel to the fibers 41 of the surface layer 42 to form an electronic representation of the surface of the composite material. The scanner generates an electrical signal that divides the surface into a grid that forms an electrical representation of the scanned surface. Each individual grid element, or pixel, is represented by a value relative to the amount of reflected light the head 13 detects.

As the light from the scanner head 13 illuminates the surface layer fibers 41, most of the light is reflected away from the scanner 12 or absorbed by the fibers 41 of the surface layer 42 so that the surface layer 42 appears black (little or no reflected light is detected). It has been found that more reflected light is detected from the lower layer 40 through the gaps 44, 46. Thus, by scanning in a direction substantially parallel to the fibers 41, the scanner output has higher light intensity values (i.e., the surface is represented by pixels having higher values) when the scanner encounters a gap than it does when the scanner encounters surface fibers.

Figure 3B:
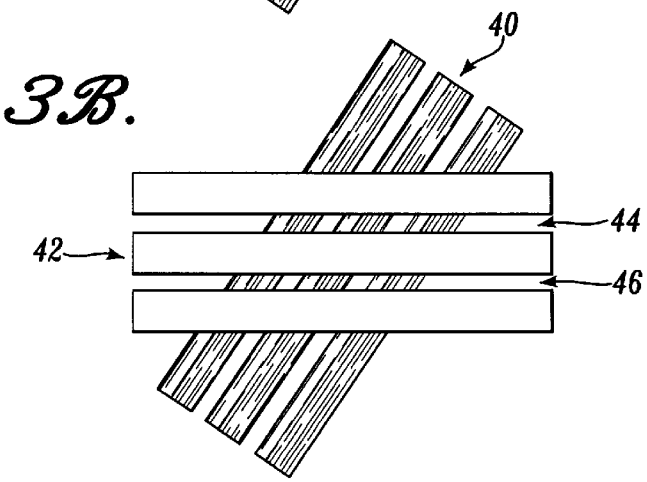
FIG. 3B is a diagrammatic top plan of the composite layers of FIG. 3A, as viewed by an optical scanner.

The composite material layers of FIG. 3A are shown in FIG. 3B as "seen" by the scanner 12 and as represented by the scanner output. Because the light is generally absorbed or reflected away from the scanner head 13 when it encounters the surface layer 42 but is reflected by the lower layer 40 so that it is received by the scanner 12, the gaps 44, 46 are differentiated from the fibers 41 on the surface layer 42.

In one embodiment, the scanner 12 is a LightningScan®Pro 256 hand-held scanner produced by Thunderware, Inc. of Orinda, Calif. The scanner 12 is connected via cable 14 to the SCSI port of the computer 16, which in the preferred embodiment is a MacIntosh Power Book operating under system 7.0 A conventional software driver interprets the scanner output to produce an electronic bit-mapped image.

The scanner 12 includes wheels 17 (shown diagrammatically in FIG. 1) on each side of the scanner head 13 that contact the surface to be scanned. As the scanner head 13 is passed across the surface, the scanner interprets the speed of rotation of the wheels 17 and adjusts the sampling rate accordingly. In this fashion, the scanner produces a bit-mapped image having pixels that represent approximately equal dimensions of the surface being scanned.

The scanner 12 can have a scanning width of four inches and a scanning resolution of 400 dots per inch (dpi), so that the scanning width is divided into 1600 pixels. Because the fibers 41 are typically ⅛ inch wide, the fibers 41 will have a width of approximately 50 pixels. Those skilled in the art will recognized that the scanner 12 may have a variety of scanning widths and resolutions consistent with the present invention.

In addition to having a variety of possible scanning resolutions, the scanner 12 may quantize the intensity of scanned image into a variety of possible ranges. In the preferred embodiment, the scanner 12 is capable of scanning 256 levels of gray. As a result, each pixel will have an associated intensity value between 0 and 255, with values closer to 0 indicating very little light was detected by the scanner head 13 and values closer to 255 indicating a greater amount of light detected.

Figure 4:
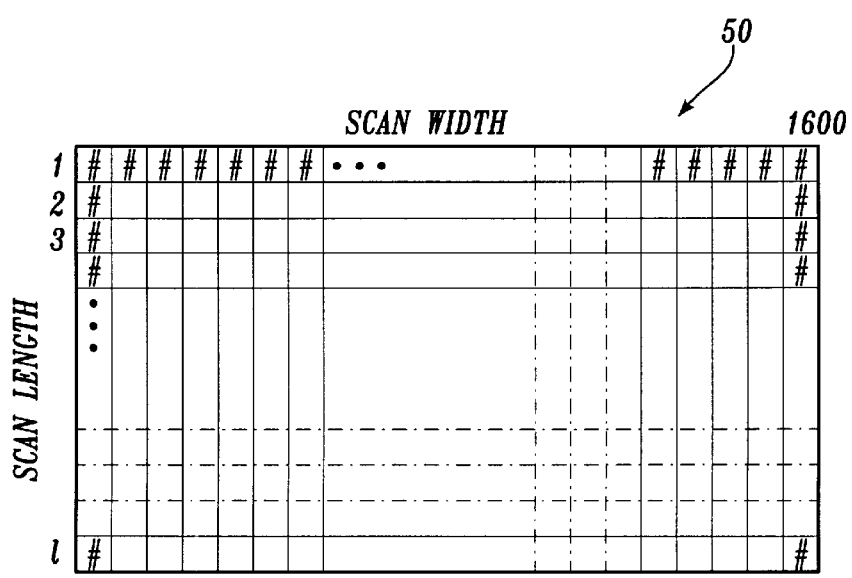
FIG. 4 is a representation of a raw data array for storing scanned pixel values determined by an optical scanner in accordance with the present invention.

To ensure that the scanner 12 scans in a direction parallel to the fibers of the surface layer 42, the scanner 12 is drawn along a straight edge or ruler. As the surface layer 42 is scanned, the values for each pixel are received from the software driver and stored in a raw data array 50 in the computer 16, represented in FIG. 4. The raw data array 50 is a two-dimensional array having a width equal to that of the scanner width, measured in pixels. Thus, in the preferred embodiment the width is four inches times 400 dots per inch, or 1600 pixels. The length of the raw data array 50, represented by the reference character l in FIG. 4, is variable and is determined by the length of composite material that is scanned. For example, by scanning an eight-inch long section of composite material, a raw data array 50 having a width of 1600 pixels and a length of 3200 pixels would be created and stored in the computer memory. For each pixel, the associated intensity value (represented as "#" in FIG. 4) is stored. The raw data array 50 may also be stored in storage 26 for later analysis.

Representations of the scanned composite surface stored in the raw data array 50 are also displayed on the display 30 of the computer 16. Each pixel value is assigned a shade of gray relative to the intensity value of that pixel and, therefore, the amount of reflected light detected by the scanner head 13 at the corresponding location on the surface of the composite material. Although shades of gray are used in the preferred embodiment, those skilled in the art will recognize that shades of other colors or combinations of colors may be used to display the electronic representation of the scanned surface. Further, the numerical values representing the amount of light received by the scanner may be displayed without converting the values into shades of gray.

Depending on the size of the scanned surface and, therefore, the length l of the raw data array, the entire raw data array may not fit on the display 30 at once. By using the pointer 29 or the keyboard 28, the display 30 can be adjusted or "scrolled" to display different portions of the raw data array 50 in a manner that is well-known in the art. In addition, the displayed image may be magnified, increasing the size of the pixels as they are displayed on the screen. Any gaps 44, 46 that are present between the fibers 41 are then easily detected because they are far more visible when viewing the display 30 than when viewing the composite material itself In addition, the size of the gaps may be determined by multiplying the number of pixels of gap times the number of inches per pixel.

Figure 5:
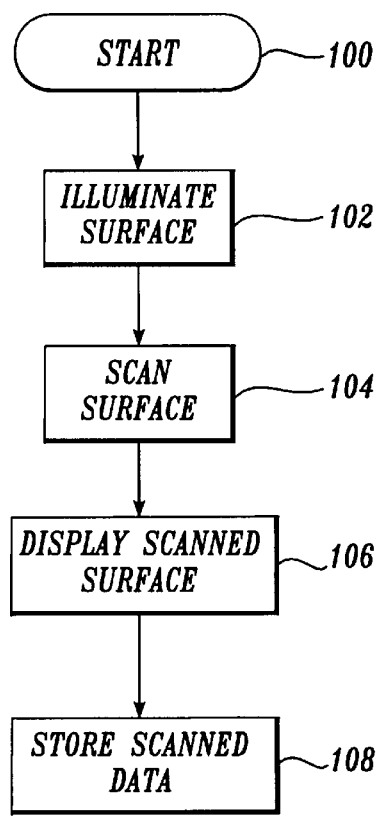
FIG. 5 is a flow chart illustrating the overall logic used to scan and display a composite lay-up material.

The overall logic employed by the present invention to scan and display a composite lay-up material may be summarized with reference to FIG. 5. The logic begins at a block 102 where the surface of the composite material is illuminated by the light source. The logic then proceeds to a block 104 where the surface is scanned by detecting the light that is reflected by the surface. In a block 106, the bit-mapped image generated by the scanner 12 is displayed on the display 30. In a block 108, the scanned bit-mapped image is stored for later retrieval and analysis.

Figure 7:
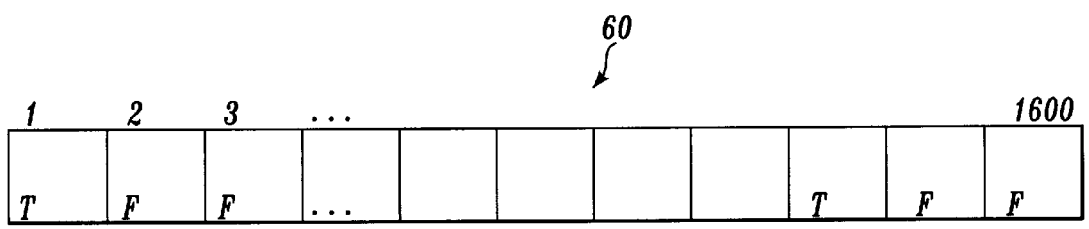
FIG. 7 is an exemplary pixel gap data array.
Figure 6:
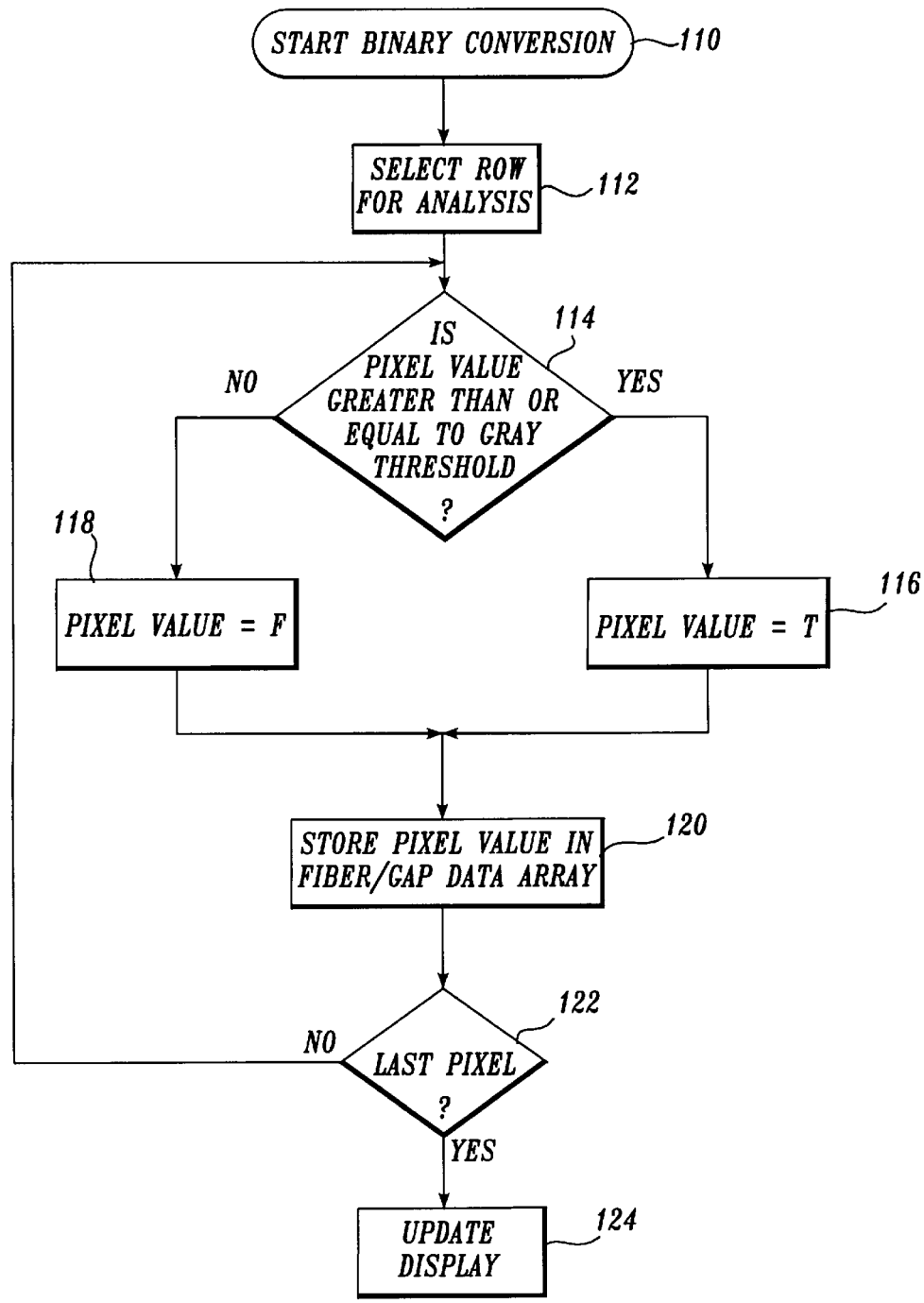
FIG. 6 is a flow chart illustrating the logic used to convert a selected scanned row to a binary representation.

Once the data has been scanned and displayed on the display 30, it may be analyzed in greater detail for the presence of laps and gaps. First, a row is selected for more detailed analysis. The row is selected by noting from the display a particular row having a lap or gap. The analysis begins by converting the pixel intensity values for the chosen row to binary values representing either gap or fiber material. The logic employed by the present invention to convert a selected row to a binary representation is illustrated with reference to FIG. 6. The logic begins with block 112, where a single row of the raw data array 50 is selected using either the keyboard 28 or pointer 29. Although only one row is selected, any number of rows may be selected, consistent with the present invention. The raw data intensity value for each pixel in the selected row is then converted to a binary value representing the presence of either a gap or fiber material at each pixel. More specifically, at block 114 the conversion is performed by comparing each pixel value to an adjustable gray threshold value that is used to distinguish fibers 41 from gaps 44, 46. In the preferred embodiment, the gray threshold value is 65. Raw scanned values from the chosen row of the raw data array 50 that are greater than or equal to the threshold value are determined to be gaps, while raw scanned values that are less than the threshold value are determined to be fiber material. While comparing each raw pixel value to the threshold value, each pixel is assigned a binary value representing either fiber or gap. The logic proceeds to block 116 for values above the threshold value which are designated "T" (fiber="true") or to block 118 for values below the threshold value which are designated "F" (fiber="false"). In either case, the logic proceeds to block 120 in which the binary value, T or F, is stored in a fiber/gap data array described below with reference to FIG. 7. Proceeding to block 122, this binary conversion process continues until the fiber/gap data array is filled. The fiber/gap data array will have the same width as the raw data array 50 and a length of one pixel. Therefore, in the preferred embodiment, the fiber/gap data array 60 has dimensions of one pixel by 1600 pixels and contains the converted binary values, T or F, for each pixel. The fiber/gap data array 60, as with all arrays discussed herein, may be displayed on the display 30 and stored in storage 26. An exemplary fiber/gap data array 60 is shown in FIG. 7.

After the fiber/gap data array 60 has been produced, the logic proceeds to block 124 to update the display 30 to represent the chosen row in a binary form. In the preferred embodiment gaps (or "F" values) are displayed as red pixels and fibers (or "T" values) are displayed as black pixels. Those skilled in the art will recognize that fibers and gaps (Ts or Fs) may be represented by using any colors or shades that will allow the fibers and gaps to be visually discernible. The binary representation on the display makes the presence of gaps readily visible.

Figure 9:
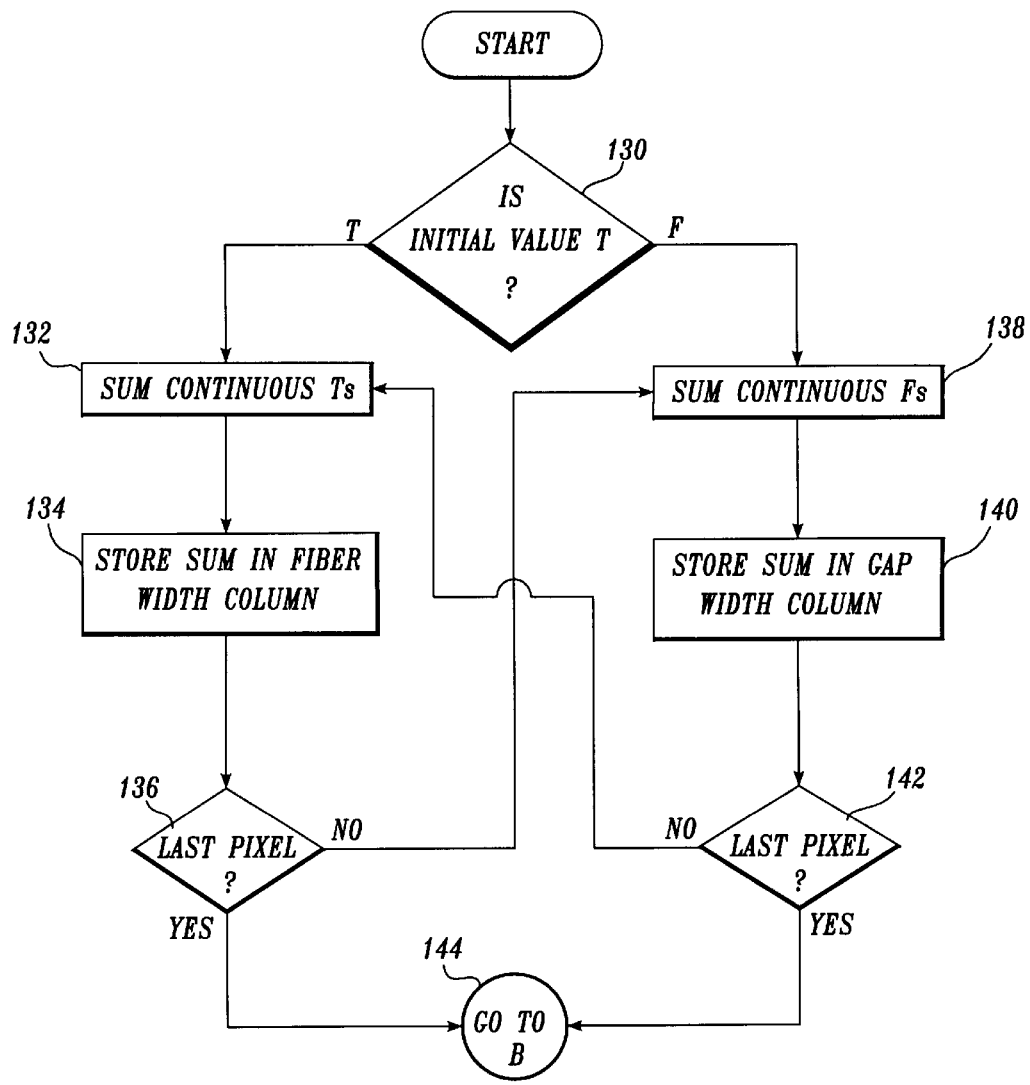
FIG. 9 is a flow chart illustrating the logic used to produce a width data array.

The fiber/gap data array 60 is then used to produce a width array 70, represented in FIG. 8A. The purpose of the width array 70 is to form an array of pairs of detected fiber widths and adjacent gap widths. Thus, the width array 70 contains two columns, one for gap widths and one for corresponding fiber widths. The logic employed to produce the width array 70 is illustrated in FIG. 9. Beginning at a block 130, the initial pixel designation from the fiber/gap data array is analyzed to determine whether it is a T or an F. If it is a T, the logic proceeds to a block 132 where consecutive Ts are summed until an F is encountered. At that point, the logic proceeds to a block 134 where the number of consecutive Ts is entered in the first row of the width array 70, under the column for fiber widths. The logic then proceeds to a block 136 to determine whether the pixel gap data array has been exhausted. If not, the logic proceeds to a block 138. Consecutive Fs are then summed until a T is encountered. At that point, the logic proceeds to a block 140 where the number of consecutive Fs is entered in the first row of the width array, under the column for gap widths. The logic then proceeds to a block 142 to determine whether there are pixels remaining to be analyzed in the fiber/gap data array. If there are values remaining, the logic returns to block 132 where consecutive Ts are then counted as previously described, with the number entered in the next row under the fiber width column. This process continues until the entire fiber/gap data array 60 has been counted. The resulting width array 70 will contain pairs of gap widths and fiber widths, arranged in two columns.

Figure 10:
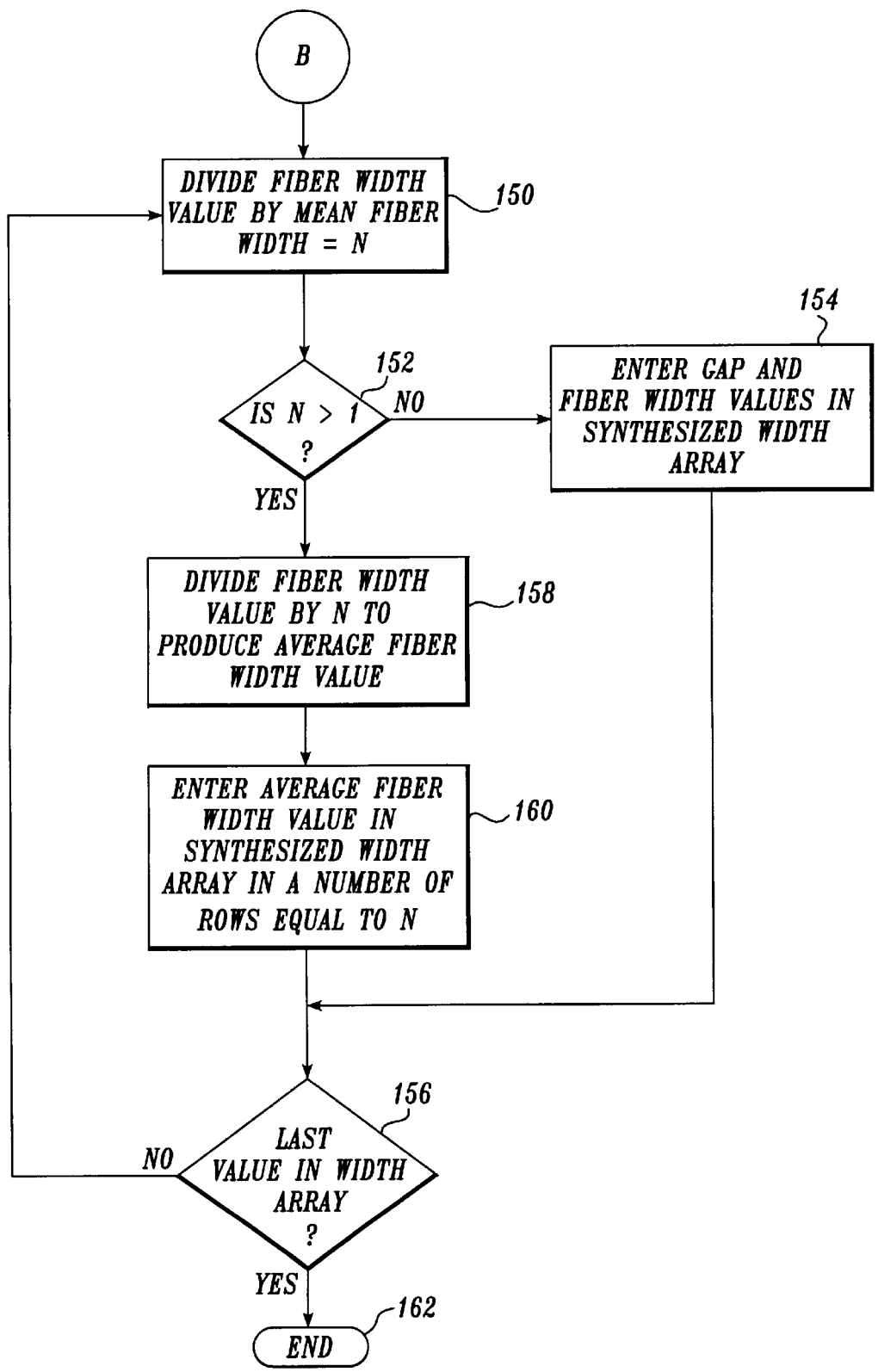
FIG. 10 is a flow chart illustrating the logic used to produce a synthesized data array.

In some cases, the fibers may overlap or may be so near each other that there is no gap between fibers. An overlap or the absence of a gap will appear on the display 30 as a continuous run of fiber material without the presence of gaps. Thus, both when looking at the composite material visually and when viewing the scanned image on the display 30, it is difficult to determine whether there is truly an overlap or whether two fibers 41 are merely adjacent to and touching each other. This difficulty is addressed by converting the width array 70 into a synthesized width array 72, represented in FIG. 8B. In converting the width array 70 into the synthesized width array 72, sums of continuous pixels representing fiber material are compared to the mean fiber width value to determine whether fibers are overlapping. The logic used to produce the synthesized width array is illustrated in FIG. 10. The logic begins at a block 150 where the value from the first row of the fiber width column of the width array 70 is divided by the mean fiber width and rounded to the nearest whole number. The mean fiber width is a pre-established value that represents the expected width of the fibers. In the preferred embodiment, the mean fiber width is ⅛ inch, or 50 pixels. The result N from dividing the value from the fiber width data array 70 by the mean fiber width is the presumed number of fibers that are adjacent or overlapping.

The logic proceeds to a block 152 to evaluate the result of the division in block 150. If the presumed number of fibers N is 1, the logic proceeds to a block 154 where the value from the measured fiber width column of the width array 70, and its corresponding gap width value, are entered in the two columns of the first row of the synthesized width array 72. If the presumed number of fibers N is greater than 1, the logic proceeds to a block 158 where the value from the fiber width column of the width array 70 is divided by the presumed number of fibers N, so that an "average fiber width" is produced. The logic next proceeds to a block 160 where the average fiber width is entered in the fiber column of the synthesized width data array 72 in a number of rows equal to the presumed number of fibers N. Following blocks 154 and 160, the logic proceeds to a block 156 to determine whether there are values in the width array remaining to be analyzed. If there are values remaining, the logic returns to block 150.

This process may be better understood with reference to FIGS. 8A and 8B. As seen in FIG. 8A, an exemplary width data array 70 may contain a value of 90 in the fiber width column. If the fiber width value of 90 from the fiber width data array 70 is divided by the mean fiber width of 50, the presumed number of fibers N is 2. As a result, two fibers are assumed to be included in the continuous run of 90 pixels represented by the value of 90 from the fiber width data array 70. Because the synthesized width array 72 is an array of fibers and corresponding gaps, the value of 90 is divided by 2 (the presumed number of fibers) to yield a value of 45, which represents the average fiber width for the two presumed fibers in the continuous run of 90 pixels. The value 45 is then entered in two consecutive rows under the fiber column of the synthesized width array 72 as shown in FIG. 8B, one entry for each presumed fiber. The gap width value associated with the measured fiber width value of 90 is stored in the first row of the gap width column of the synthesized data array 72. Because there is no measured gap between the two fibers presumed to exist in the run of 90 fiber pixels, the symbol "*" is entered in the gap column in the row associated with the second synthesized fiber.

From the synthesized width array 72, gaps and laps can be readily found and measured. The individual fiber and gap columns can be quickly analyzed to search for abnormalities. Thus, the gap column can be compared against a gap tolerance value to determine whether any of the gaps are too large. Likewise, the synthesized width data array 72 can be analyzed for the presence of laps. There are two indicators that will signal the likely presence of an overlap. First, the presence of an unusually large gap is normally an indication that the fibers on either side of the gap are overlapping. Second, long runs of fiber material (many consecutive Ts) indicates either an overlapping or touching fibers. From the synthesized width data array 72, the long continuous runs of fiber have been divided into asterisks ("*") and average fiber widths. If the estimated average fiber widths from these long continuous runs are less than the expected mean fiber width, it is probably due to an overlap.

Figure 11:
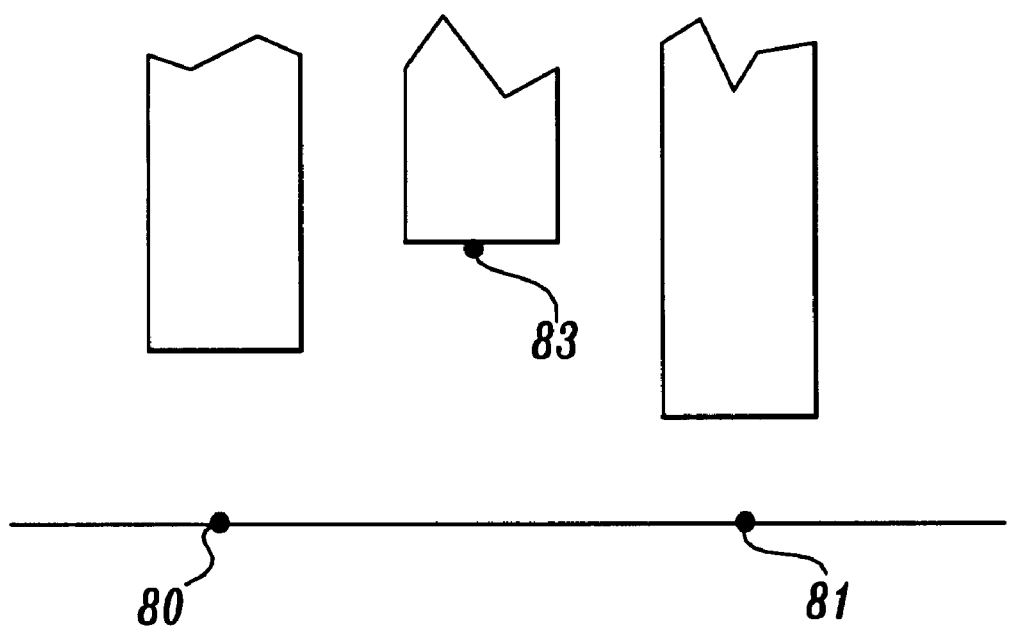
FIG. 11 is an enlarged representation of a scanned display showing three fibers.

In addition to detecting laps and gaps, the lap/gap detector of the present invention may be used to determine distances between points on the display, and therefore the composite material. This feature is especially useful when estimating whether fiber material was placed sufficiently close to a reference line, such as a line indicating a hole or a cut to be made in the composite material. Likewise, this feature may be used to measure distances between laps or gaps. Referring to FIG. 11, an enlarged display with three runs of fiber is shown. By using the keyboard 28 or pointer 29, two points 80, 81 on the display are selected. The line connecting the two points 80, 81 is shown on the display, representing the desired stopping point for the fiber material. To determine whether the fibers are sufficiently close to the line between the two points 80, 81, a point 83 on the end of one of the fibers is selected. The perpendicular distance between the point 83 on the end of the fiber and the line is then calculated to determine whether the fiber is close enough to the line.

Figure 12:
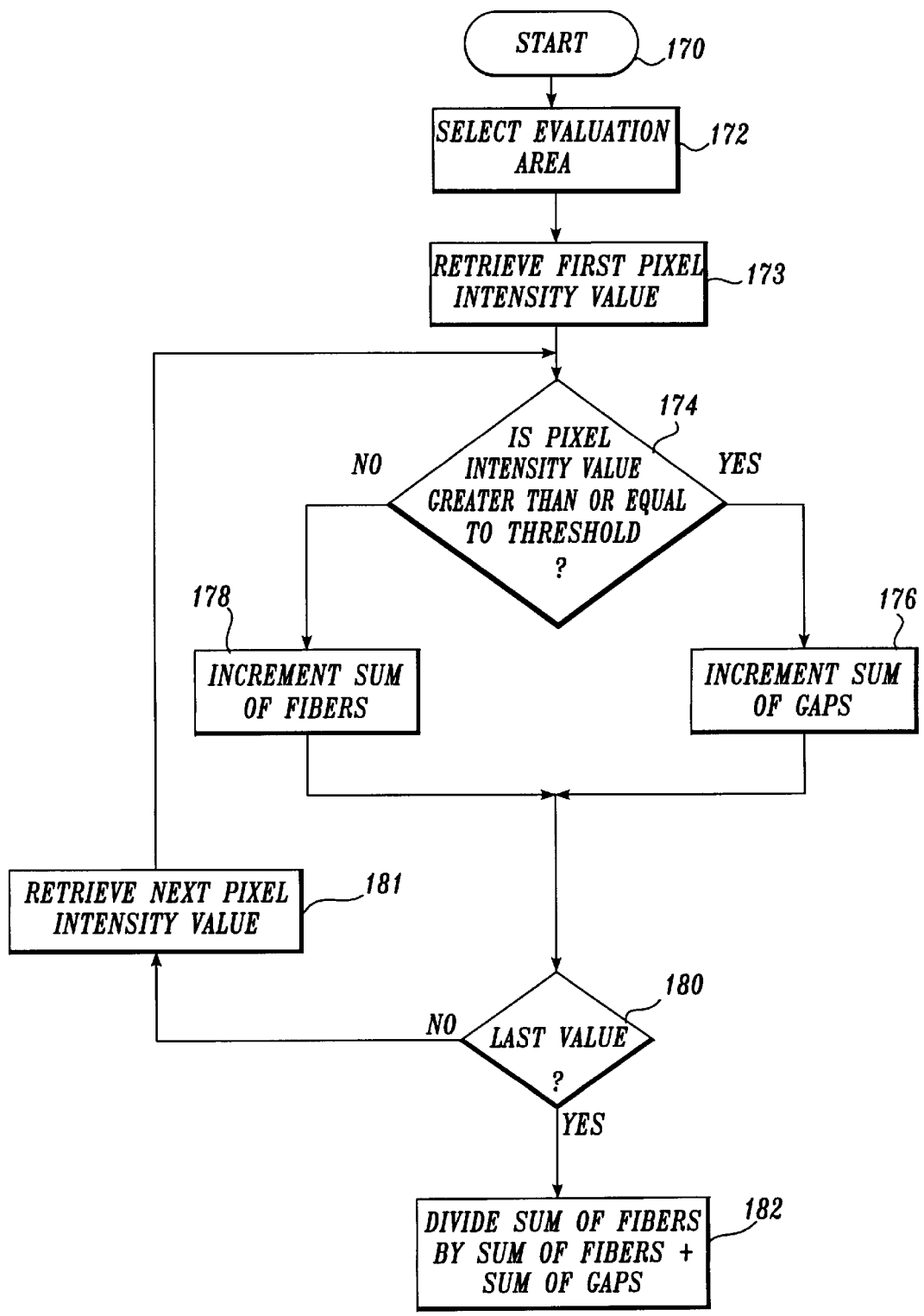
FIG. 12 is a flow chart illustrating the logic used to determine the percentage of fiber coverage.

The lap/gap detector of the present invention also calculates the density of the scanned image. In other words, the lap/gap detector determines the percentage of the surface area of the scanned image that is covered by fiber material. The logic used to determine the percentage of coverage is illustrated in FIG. 12. The image density determination begins at a block 172 by establishing an evaluation area. The evaluation area is selected by using the keyboard 28 or pointer 29 and may be as small as one pixel or as large as the entire raw data array 50. Once the evaluation area is established, the corresponding portion of the raw data array 50 is used to determine the image density. The logic proceeds to a block 173 where the intensity value for the first pixel in the evaluation area is retrieved. In a block 174, the intensity value is compared to the gray threshold value to determine whether it represents a fiber or a gap. If the value is greater than or equal to the threshold, the logic proceeds to a block 176 where the sum of gap values is incremented. If, on the other hand, the value is less than the gray threshold, the logic proceeds to a block 178 where the sum of fiber values is incremented. From blocks 176 and 178 the logic proceeds to block 180 to determine whether there are pixels remaining the evaluation area. If there are pixels remaining in the evaluation area, the logic proceeds to a block 181 where the next value is retrieved and the evaluation process is repeated. Once there are no pixels remaining, the logic proceeds to block 182. The image density, or percentage of the evaluation area that is covered by fibers, is determined by dividing the total number of fiber pixels by the total number of pixels in the evaluation area.

The present invention offers significant advantages over the prior art method of visually scanning composite lay-up materials for the presence of laps and gaps. By using the present invention, a composite surface is scanned and displayed in a manner that allows laps and gaps to be readily discovered. An electronic representation of the composite surface is also analyzed to measure gap widths, determine the presence of overlapping fibers, measure the distance between points on the scanned surface, and calculate the percentage of the surface that is covered by fibers. The electronic representation of the composite surface may also be stored for later analysis.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An apparatus for detecting laps and gaps between fibers of a composite material, comprising:
   (a) a light source for illuminating the surface of the composite material;
   (b) a scanner associated with the light source for scanning the surface of the composite material to form an electronic representation of the scanned surface wherein the representation of the surface is divided into pixels, each pixel having an intensity value relative to the amount of light detected when scanning a corresponding portion of the surface;
   (c) a display associated with the scanner for displaying the representation of the scanned surface so that laps and gaps are visible;
   (d) a processing unit; and
   (e) a memory coupled to the processing unit, the memory at least temporarily storing the pixel intensity values and storing program instructions that control the processing unit, execution of the program instructions on the processing unit comprising:
      (i) converting the pixels for at least part of the scanned surface to a binary representation indicating that either a gap or fiber material is present at the location corresponding to that pixel;
      (ii) summing alternately the number of continuous converted pixels representing gaps and the continuous converted pixels representing fiber material to form values representing the number of continuous pixels of fiber and gap material; and
      (iii) comparing the sums of continuous converted pixels representing fiber material with a mean fiber width value.

2. An apparatus for detecting laps and gaps between fibers of a composite material, comprising:
   (a) a light source for illuminating the surface of the composite material;
   (b) a scanner associated with the light source for scanning the surface of the composite material to form an electronic representation of the scanned surface wherein the representation of the surface is divided into pixels, each pixel having an intensity value relative to the amount of light detected when scanning a corresponding portion of the surface;
   (c) a display associated with the scanner for displaying the representation of the scanned surface so that laps and gaps are visible;
   (d) a processing unit; and
   (e) a memory coupled to the processing unit, the memory at least temporarily storing the pixel intensity values and storing program instructions that control the processing unit, execution of the program instructions on the processing unit comprising:
      (i) converting the pixels for at least part of the scanned surface to a binary representation indicating that either a gap or fiber material is present at that pixel;
      (ii) summing alternately the number of continuous converted pixels representing gaps and the continuous converted pixels representing fiber material to form values representing the number of continuous pixels of fiber and gap material; and
      (iii) comparing the sums of continuous converted pixels representing gaps with a gap tolerance value.

3. An apparatus for detecting laps and gaps between fibers of a composite material, comprising:
   (a) means for scanning the surface of the composite material to form an electronic representation of the scanned surface wherein the surface is divided into pixels, each pixel having an intensity value relative to the amount of light received when scanning a corresponding portion of the surface;
   (b) means associated with the scanner for displaying the representation of the scanned surface so that laps and gaps are visible;
   (c) a processing unit; and
   (d) a memory coupled to the processing unit, the memory at least temporarily storing the pixel intensity values and storing program instructions that control the processing unit, execution of the program instructions on the processing unit comprising:
      (i) converting the pixels for at least part of the scanned surface to a binary representation indicating that either a gap or fiber material is present at the location corresponding to that pixel;
      (ii) summing alternately the number of continuous converted pixels representing gaps and the continuous converted pixels representing fiber material to form values representing the number of continuous pixels of fiber and gap material; and
      (iii) comparing the sums of continuous converted pixels representing fiber material with a mean fiber width value.

4. An apparatus for detecting laps and gaps between fibers of a composite material, comprising:
   (a) means for scanning the surface of the composite material to form an electronic representation of the scanned surface wherein the surface is divided into pixels, each pixel having an intensity value relative to the amount of light received when scanning a corresponding portion of the surface;
   (b) means associated with the scanner for displaying the representation of the scanned surface so that laps and gaps are visible;
   (c) a processing unit; and
   (d) a memory coupled to the processing unit, the memory at least temporarily storing the pixel intensity values and storing program instructions that control the processing unit, execution of the program instructions on the processing unit comprising:
      (i) converting the pixels for at least part of the scanned surface to a binary representation indicating that either a gap or fiber material is present at the location corresponding to that pixel;
      (ii) summing alternately the number of continuous converted pixels representing gaps and the continuous converted pixels representing fiber material to form values representing the number of continuous pixels of fiber and gap material; and
      (iii) comparing the sums of continuous converted pixels representing gaps with a gap tolerance value.

* * * * *